United States Patent [19]

Coplin

[11] Patent Number: 4,917,673
[45] Date of Patent: Apr. 17, 1990

[54] ASSEMBLY FOR THE PROTECTION AGAINST INADVERTENT PUNCTURE BY MEDICAL NEEDLES

[76] Inventor: Allan J. Coplin, 3340 SW. 59th St., Ft. Lauderdale, Fla. 33312

[21] Appl. No.: 264,971

[22] Filed: Oct. 31, 1988

[51] Int. Cl.⁴ ............................................. A61M 5/00
[52] U.S. Cl. ..................................... 604/198; 604/263
[58] Field of Search ............... 604/198, 263, 110, 187, 604/195, 136, 192

[56] References Cited

U.S. PATENT DOCUMENTS 4,795,432  1/1989  Karczmer ........................... 604/110
4,813,940  3/1989  Parry ................................... 604/198

FOREIGN PATENT DOCUMENTS 2202747  10/1988  United Kingdom ................. 604/198

*Primary Examiner*—John D. Yasko
*Attorney, Agent, or Firm*—Malloy & Malloy

[57] ABSTRACT

A protection assembly to protect medical personnel from being inadvertently punctured by the pointed end of a medical needle of the type normally associated with a syringe, catheter assembly or I.V. administering structure. An elongated sleeve like shield is selectively positionable from a non-covering position to a covering position relative to the needle by manipulation of the shield sleeve, using a single hand of the user of the subject assembly, due at least in part to the existence of a biasing structure disposed to normally bias the shield towards the covering position.

17 Claims, 2 Drawing Sheets

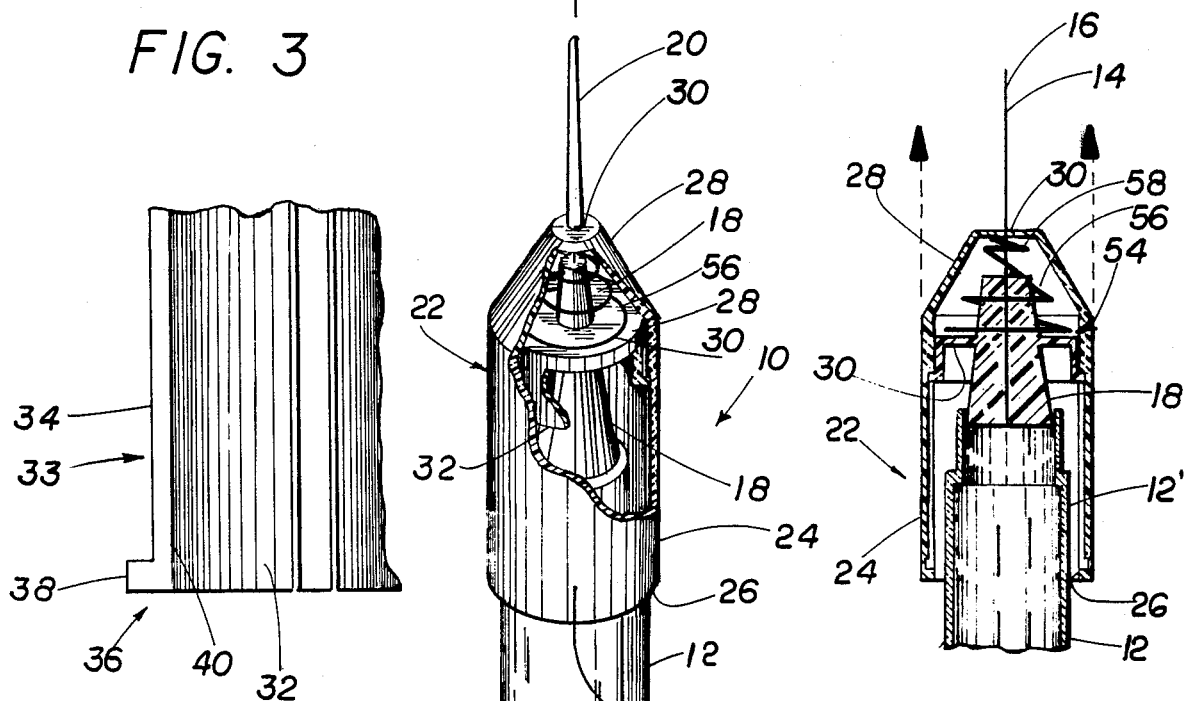

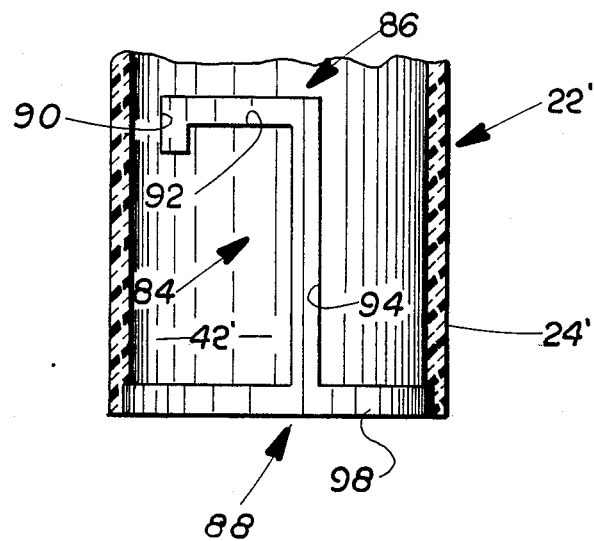
FIG. 8
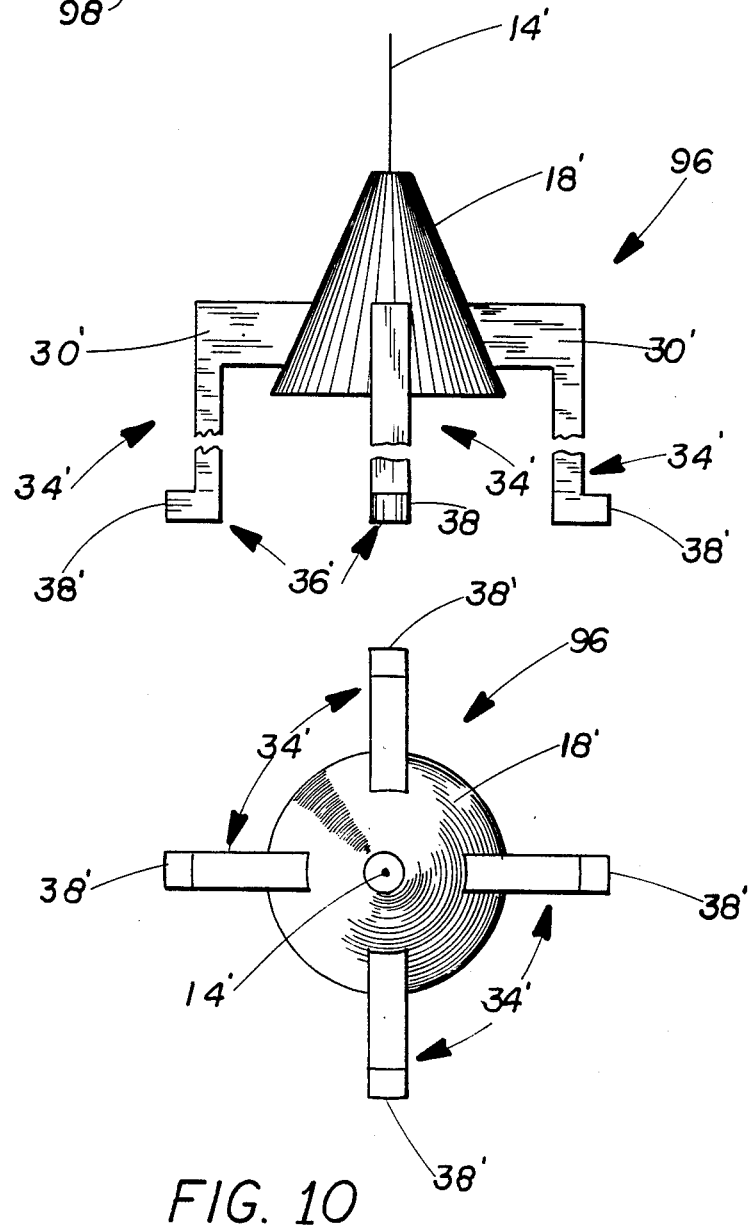
FIG. 9
FIG. 10

ASSEMBLY FOR THE PROTECTION AGAINST INADVERTENT PUNCTURE BY MEDICAL NEEDLES

BACKGROUND OF THE INVENTION

1. Field of the Invention

The present invention relates to a protection structure capable of covering a medical needle after use, such as when it is withdrawn from the patient's body, thereby preventing inadvertent contact and penetration of the sharpened end of the needle with medical personnel handling the needle.

2. Description of the Prior Art

Use of needles in the medical profession for transferring bodily fluids both into and from the human body is of course extremely widespread and a common practice in patient care. Due to the advances in modern medical technology, numerous structural modifications have been made with the intravenous needle and the reservoir structure to which it is attached such as but not limited to a catheter, hypodermic syringe, I.V. administering assembly, etc. The majority of such structures presently in use are now intended and designed to be disposable after a single use in order that infectious and contagious diseases cannot be spread from one patient to another. Such disposable medical structures are also utilized in order to eliminate any sterilizing step or processes previously used with "permanent" intravenous needle structures.

In utilizing such disposable structures, proper techniques for the actual disposal of such intravenous needles have become particularly important in recent years in an effort to reduce the inadvertent spread of contagious diseases such as, but not limited to Acquired Immune Deficiency Syndrome (AIDS). The later disease is of particular concern since there is no known cure. Further, it has been scientifically established that one method of transferring the disease is through the use of intravenous needles.

Accordingly, there is a need in the medical profession and the medical instrument industry for a device capable of being used with disposable intravenous and like needles useable on a variety of medical structures which adequately and effectively protects the sharpened or pointed tip of the needle from inadvertently coming into contact, and puncturing the medical personnel operating the medical instrumentation. Of particular concern is the ability to allow the medical personnel preferably to utilize a single hand in the operative and selective positioning of a shield in overlying and covering, protecting relation to the sharpened point of the needle. Typically, prior art and present day techniques involve the inclusion of an elongated hollow hub or covering in which the needle is originally packaged. The needle is administered to the patient by first removing the hub. After injection or withdrawal of the intended fluid to or from the patient, the needle is removed and the hub is normally inserted in covering and protecting relation to the needle.

In such a procedure, both hands of the person are utilized; one to hold the syringe or like medical structure and the other to fit the shield over the needle. Such techniques and apparatus have resulted in numerous inadvertent punctures of medical personnel even when extreme care was utilized.

Accordingly, a preferred technique and apparatus would involve the personnel to utilize a single hand to operatively position a shield or like protective structure in covering relation to the needle without bringing the other hand into close proximity to the pointed end of the needle.

In an attempt to overcome certain of the above set forth problems in the medical profession, the prior art is replete with numerous structures designed for the shielding or protection of the needle, and particularly the pointed end thereof so that inadvertent punctures and contact with medical personnel would be eliminated. Problems associated with many of the prior art structures is the ineffectiveness to adequately protect medical personnel, complex structural design of such medical structures resulting in their being commercially impractical and the inability of many of the structures to be operated utilizing only a single hand of the user.

SUMMARY OF THE INVENTION

The present invention relates to a protective shield designed to be movably attached and utilized in combination with a medical instrument incorporating a fluid dispensing or receiving needle such as but not limited to a hypodermic syringe, catheter, I.V. assembly, etc. The protective assembly of the present invention includes a shield means preferably in the form of an elongated hollow interior sleeve or tube having its outer most end substantially closed. The closed end however does have an aperture integrally formed therein of sufficient transverse dimension to concentrically surround the needle and allow passage thereof through the aperture when the shielding sleeve moves along the length of the needle from a non-covering position to a covering position.

The non-covering position is defined by the shield disposed in a somewhat retracted position leaving the pointed free end of the needle and a majority of the length thereof free for penetration into a patient's body. Conversely, the covering or protecting position of the shield sleeve is defined by its positioning in an outwardly extended disposition from a position generally adjacent the needle mount to an outer pointed end of the needle. In such a covering position, the closed end of the shield covers the pointed end of the needle in a protecting relation thereto.

A locking means is incorporated in the subject assembly to assure that the shield sleeve is removably maintained, selectively either in the covering position or the non-covering position. Further, the locking means incorporates preferably a plurality of flexible material finger structures disposed transversely or radially outward from and adjacent to one needle mount. The fingers have projecting portions preferably formed at their distal end. A projecting portion of each finger extends outwardly from the length of the finger into sliding and removably locking engagement with cooperative structures formed on the inner surface of the shield sleeve. Such cooperative structural features on the inner surface may be defined by track means including a plurality of integrally formed, elongated tracks at least equal in number to the number of fingers and disposed in cooperative engagement with the aforementioned projecting portions thereof. In a preferred embodiment to be described in greater detail hereinafter, opposite ends of each of the tracks are structured and configured to receive the projecting portions of the correspondingly disposed fingers such that a locking inner engagement may occur therebetween. Therefore, initially the shield sleeve is disposed in its non-covering position wherein the projecting portions of each of the plurality of fingers removably but lockingly engage the correspondingly positioned ends of the cooperative track structures. Depending upon the specific configuration and/or structure of the tracks relative to the projecting portions which they engage, the medical personnel utilizing the instrument merely has to rotate and/or properly manipulate the shield relative to the needle, needle mount and/or remaining body portion of the medical instrument on which the needle is mounted in order to release the fingers from their initially locked position within the tracks.

A biasing means is disposed on the interior of the sleeve in biasing engagement with a portion thereof such as preferably the closed end portion. Upon release of the fingers from the locking ends of the tracks, the biasing means serves to force outward travel of the shield means coaxially relative to the needle and along its length. The longitudinal dimension of the sleeve as well as the dimension and configuration of the biasing means extends the sleeve in completely covering relation along the length of the needle and in overlying covering relation to the pointed end thereof. At such location, the projecting portions of each of the fingers serves to engage an opposite end of the respective tracks and thereby lockingly engage and maintain the shield sleeve in the aforementioned covering and protected position relative to the pointed end of the needle.

The invention accordingly comprises the features of construction, a combination of elements, an arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a perspective view in partial cut-away of the protective assembly of the present invention mounted on a medical instrument incorporating an intravenous or similarly structured needle.

FIG. 2 is a sectional view in partial cut-away of the embodiment of FIG. 1 taken along line 2—2 thereof and further indicating a shield portion of the subject invention both in a covering and non-covering position.

FIG. 3 is an exterior view in partial cut-away along line 3—3 of FIG. 5.

FIG. 4 is an interior detail view in partial cut-away along line 4—4 of FIG. 6.

FIG. 5 is a transverse sectional view of one portion of the protection assembly of the present invention.

FIG. 6 is a transverse sectional view of another cooperative component of the subject assembly.

FIG. 7 is a sectional view in partial cut-away along line 7—7 of FIG. 4.

FIG. 8 is an internal sectional view in partial cut-away of another embodiment of the present invention.

FIG. 9 is top view of yet another embodiment of the present invention.

FIG. 10 is a front elevational view of the embodiment of FIG. 9.

Like reference numerals refer to like parts throughout the several views of the drawings.

DETAILED DESCRIPTION OF THE PREFERRED EMBODIMENT

As shown in FIGS. 1 through 7, the present invention is directed towards a protection assembly generally indicated as 10 of the type intended to be used with a medical instrument or structure 12 such as a hypodermic syringe or the like. The medical instrument 12 specifically is of the type designed to be interconnected in fluid communication with a penetrating needle 14 having a sharpened end or tip 16 used to enter a patients body for the delivery or withdrawal of fluids. Accordingly, the needle 14 is mounted on any type of standard or conventional needle mount 18 itself being connected to a fluid chamber 12'. It should be emphasized that the medical instrument 12 could be any of a variety of commonly known and frequently utilized structures such as a hypodermic syringe, catheter, I.V. set-up, etc.

In the embodiment of FIG. 1, the medical instrument 12 is shown in a position immediately prior to use wherein a disposable protecting cap or hub 20 is initially positioned in covering relation to the needle support 14 so as to maintain the needle in a sterile condition prior to use. Immediately prior to use, the hub 20 is removed from the needle 14 and discarded.

An important structural feature of the present invention includes a shield means 22 primarily defined by an elongated sleeve or tubular structure 24 having one open end as at 26 of sufficient transverse dimension to fit about and in surrounding relation to the exterior of the medical instrument or structure 12 as shown in both FIGS. 1 and 2.

In addition, the sleeve 24 has a substantially closed end as at 28 which includes an integrally formed, substantially centrally disposed aperture 30 having a sufficient transverse dimension to allow passage therethrough of the entire length of the needle 14 as the shield sleeve 24 moves into a covering position as indicated in phantom lines in FIG. 2 from a non-covering position as represented in solid lines in FIG. 1.

In the non-covering position shown in both FIGS. 1 and 2 in solid lines, it is clearly seen that the shield sleeve 24 has a hollow configuration along its length so as to substantially surround and at least partially enclose the needle mount 18 and an upper portion of the medical instrument 12 to which the needle is attached.

Provided on the interior of the shield sleeve 24 but securely attached adjacent to the needle mount 18 and/or being an integral part thereof, is a locking means generally indicated as 33. In a preferred embodiment, the locking means includes in a transversely or radially extending disk 30 being attached to the needle mount 18. Further, the locking means 33 includes a depending skirt portion 32 depending downwardly from the disk or base portion 30. At least one but preferably a plurality of flexible material fingers indicated as 34 are attached either fixedly or integrally to the locking means and preferably extending along the length of the skirt portion 32 also in depending relation to the disk 30. In a preferred embodiment, each of the fingers 34 are attached only at an upper most end thereof such that the majority of the length of each finger 34 is spaced from the adjacently positioned wall of the skirt 32 so as to allow movement of a majority of the length of each of the fingers 34 and particularly the distal end thereof generally indicated as 36 and defined by an outwardly projecting portion 38 (see FIGS. 3 and 5). In FIG. 3 only a single finger structure 34 is shown. Suffice it to say that each of the fingers are similarly structured and spaced from an adjacent side wall portion of the skirt 32 by elongated slots 40 extending along the majority of the length on each side of the finger 34. The outwardly projecting portion 38, defining the distal end 36 of each finger 34, extends outwardly a sufficient distance from the outer surface of the skirt 32 to cooperate with a track means integrally formed on the interior surface 42 of the shield sleeve 24 as best shown in FIGS. 4 and 6. The track means comprises at least one but preferably a plurality of tracks generally indicated as 44 preferably integrally formed to recess inwardly into the inner surface 42 of the shield sleeve 24. Preferably the number of tracks 44 are at least equal to the number of fingers 34. Due to the outward extension of the projection portion 38 of each finger, such projecting portion 38 effectively "rides" in and or slides along the length of the correspondingly positioned track 44. Further, a first inner end of each track 44 being generally indicated as 48 is formed to removably but lockingly receive a corresponding projecting portion 38 of a finger 34 as is a second, oppositely disposed end thereof generally indicated as 50. With regard to FIG. 7, both the entire length of the track 44 is recessed inwardly into the surface 42. However, at least one end as at 50 includes a receiving socket 54 recessed into the inner surface 42 of sleeve 24 even a greater distance than the majority of the length of the track 44 as clearly shown. The transverse dimension of both the track 44 and a correspondingly positioned projecting portion 38 are dimensioned to allow free, sliding movement therebetween and thereby selective positioning of the shield sleeve 24 between a non-covering position shown in solid lines in FIGS. 1 and 2 and a covering position represented in phantom lines in FIG. 2. As set forth above, the non-covering position of the shield sleeve 24 allows the use of the needle 14 in the conventional fashion to supply fluids to or withdraw fluids from the patient's body. However, when the shield sleeve 24 is in its covering position, the sharpened point or tip 16 is prevented from coming into inadvertent contact with medical personnel or any user of the instrument 12 since such pointed end 16 is completely covered.

Accordingly, an important feature of the present invention is a biasing means generally indicated as 54 in the form of a spring element 56 mounted on the interior of the shield sleeve 24. The biasing spring 56 has one end as at 58 preferably engaging the inner surface of the closed end 28 while the opposite end or some portion of the spring element 56 is mounted adjacent to and in substantially anchored relation on the needle mount 18 or the outwardly extending base 30 of the locking means 33. Therefore, it should be readily apparent that the position of the sleeve 24 in its non-covering position serves to orient the biasing spring 56 into a compressed orientation. This in turn exerts a biasing force on the sleeve 24 tending it to move in an outwardly extended coaxial direction of travel relative to the needle 14 and into the aforementioned covering position of the shield sleeve 24.

However, in such non-covering position, each projecting portion 38 of each finger 34 is disposed in a first segment 58 of the track 44 substantially as represented in phantom lines in FIG. 4 and also as shown to a somewhat lesser extent in FIG. 2. The projecting portion 38' (see FIG. 4) once disposed in the segment 58 in the position shown in FIG. 4 will prevent the sleeve from being passed into the covering position in encasing relation to the needle 14 and pointed end 16 until the user of the medical instrument 12, with one hand, serves to initially move the shield sleeve 24 in the direction indicated by phantom arrow 60 and immediately thereafter, rotate the sleeve relative to the locking means 28 and accordingly each of the fingers 34 in the direction indicated by directional arrow 62. This will place each of the attendant and cooperatively disposed projecting portions of each finger 34 into the position indicated as at 38" and in aligned position with the elongated segment 64 of each track 44 (see FIG. 4). The user of the medical instrument 12 then releases his grip on the exterior of the shield sleeve 24 allowing the biasing spring 56 to drive the shield sleeve 24 outwardly along the length of the needle 14 into the aforementioned covering position. The respective projecting portions 38 will then travel along the entire length of the respective tracks 44 until such respective projecting portions reach and pass into the receiving socket 54 (see FIG. 7). Such will occur naturally due to the inherent bias or flexability of the material from which the fingers 34 are formed and due to the fact that they are spaced from the wall of the skirt 32 along a majority of their length as shown in FIGS. 2 and 3. The natural outward biasing of the fingers 34 will force the respective projections 38 into the receiving socket 54 causing the shield sleeve 24 to be locked in place in the aforementioned covering position serving to protect the pointed end 16 against any adverdent contact with medical personnel or user of the medical instrument 12.

Yet another embodiment of the present invention referring specifically to the track means indicated as 84 being integrally formed in recessed relation into the interior of the inner surface 42' of the shield means 22' defined, as in the embodiments discussed above, as the shield sleeve 24'. The track means includes an upper or inner most end as at 86 having a transverse section 92 and an end most section 90 formed similar to the end most section 58 in the embodiment of FIG. 4. The transverse section 92, however, extends away from the elongated section 94 in a different direction from that shown in FIG. 4. Further, the opposite end as at 88, of the embodiment of FIG. 8, is devoid of the receiving pocket 54 integrally formed in the end 50 of the embodiment of FIG. 4. Instead, the elongated segment 94 terminates in a continuous, annularly configured recess 98. Such recess 98 extends inwardly a greater distance into the surface 42' than does the elongated segment 94 in order to allow receipt and a somewhat locking engagement of correspondingly projecting end portions 38 of the various fingers 34 as set forth above. However, this structural configuration of the embodiment of FIG. 8 still allows the user of the assembly to selectively position the shield means 22' in the protective position relative to the needle 14 and pointed end thereof 16 using a single hand.

Yet another embodiment of the present invention is shown in FIGS. 9 and 10 wherein the locking means 96 comprises the hub mount 18' having integrally formed thereon an extending radially outward therefrom, connecting flanges 30' disposed in spaced apart relation to one another. The fingers 34' depend downwardly from respective ones of the flanges 30' and terminate at their respective distal ends 36' in the outwardly extending or projecting member 38' which travels within the track structure 44 (see FIG. 4) or track structure 84 (see FIG. 8).

Now that the invention has been described, what is claimed is:

1. A protection assembly for a needle including a needle mount designed to be used in connection with a syringe, catheter or like medical instrument, said assembly comprising:
   (a) shield means movable relative to said needle and the medical instrument and positionable between a covering and a non-covering position for selective protection of a pointed end of the needle,
   (b) said shield means including an elongated configuration and a hollow interior portion and disposed in surrounding, concentric relation to the needle,
   (c) said shield means having a sufficient longitudinal dimension to extend along the length of he needle from at least the needle mount to overlying and covering relation to the pointed end thereof when in said covering position,
   (d) said shield means comprising a sleeve structure including one end being substantially open and transversely dimensioned to concentrically surround and move relatively to an outer surface of the medical instrument when said sleeve is moved from said non-covering position to said covering position,
   (e) said sleeve comprising an opposite end being substantially closed and including a central aperture formed in said opposite end and being of sufficient transverse dimension to allow passage therethrough of the needle,
   (f) biasing means mounted adjacent the needle mount within said hollow interior portion in biasing engagement with said shield means for biasing thereof to move outwardly, coaxially along the length of the needle from said non-covering position to said covering position,
   (g) locking means mounted adjacent the needle mount and extending laterally outward therefrom into locking engagement with an interior surface of said shield means at at least two spaced apart locations along the length of said shield means,
   (h) said locking means and said interior surface cooperatively structured and disposed to removably lock said shield means selectively in either said covering or said non-covering position, and
   (i) said locking means comprising a plurality of fingers at least two of which are each disposed radially outward from the needle mount in opposed relation to one another and adjacent to and in substantially parallel relation with said inner surface of said sleeve, each of said fingers flexibly structured and movable relative to a remainder of said locking means into engaging relation with said inner surface of said sleeve at a distal end of each finger.

2. An assembly as in claim 1 wherein said biasing means comprises a spring element having a first end mounted adjacent the needle mount and extendable outwardly therefrom into outwardly biasing engagement with an inner surface of said sleeve adjacent said closed opposite end and in surrounding relation to the needle.

3. An assembly as in claim 2 wherein said spring element is disposable between a retracted position, defined by a compressed orientation of said spring element when said shield means is in said non-covering position, and an extended position defined by a outwardly extended orientation of said spring element when said shield means is in said covering position.

4. An assembly as in claim 1 wherein said locking means comprises at least one finger disposed radially outward of the needle mount and adjacent to and in substantially parallel relation with said inner surface of said sleeve, said one finger flexibly structured and movable relative to a remainder of said locking means into engaging relation with said inner surface of said shield means.

5. An assembly as in claim 2 wherein said distal end of each finger includes a projecting portion extending outwardly from a remainder of said finger into movable engagement with said inner surface of said shield means.

6. An assembly as in claim 5 further comprising a track means for guiding movement of said shield means relative to said locking means and including a plurality of track structures equal at least in number to said fingers and being elongated and integrally formed on said inner surface of said sleeve and each including a first end and a second end each cooperatively configured and disposed to lockingly receive a correspondingly disposed one of said plurality of projecting portions therein.

7. An assembly as in claim 6 wherein at least one of said first and second ends of each track structure includes a receiving socket recessed inwardly into said inner surface of said sleeve a sufficient distance to receive a corresponding one of said projecting portions therein and recessed inwardly a greater distance than a majority of the remainder of a respective one of said track structures.

8. An assembly as in claim 7 wherein an opposite one of said first and second ends relative to said receiving socket is disposed and configured to removably and lockingly engage a corresponding one of said projecting portions therein.

9. An assembly as in claim 8 wherein said receiving socket is disposed at one end of each track structure positioned closest to said open end of said sleeve, said opposite end being disposed substantially adjacent said closed end thereof.

10. An assembly as in claim 6 wherein each of said track structures is recessed inwardly into said inner surface of said sleeve along a majority of its length a sufficient distance to at least partially slidingly receive a corresponding one of said projecting portions therein.

11. An assembly as in claim 10 wherein at least one of said first and second ends of each track structure includes a receiving socket recessed inwardly into said inner surface of said sleeve to a greater depth than a majority of the remainder of a respective one of said track structures and sufficient to lockingly receive a corresponding one of said projecting portions therein.

12. An assembly as in claim 11 wherein said projecting portion of each finger is disposed in movable, biased engagement with a corresponding one of said track structures along its length and between opposite ends thereof.

13. An assembly as in claim 12 wherein each of said track structures comprises a first segment disposed substantially adjacent said closed end of said sleeve and being disposed transverse to the length thereof and a second segment extending along the length of said sleeve from said first segment towards said open end of said sleeve.

14. An assembly as in claim 13 wherein said second segment communicates with said first segment and has a greater longitudinal dimension than said first segment, said sleeve movable continuously from and along the length of said first segment to and along the length of said second segment between opposite ends of said track structure, said sleeve movable both rotationally and longitudinally relative to the needle when being positioned from said non-covering position to said covering position.

15. An assembly as in claim 1 wherein said locking means comprises at least one finger disposed radially outward from the needle mount and adjacent to and in sliding engagement with said inner surface of said sleeve, said one finger including a projecting portion flexibly structured to extend outwardly into movable engagement with said inner surface of said sleeve.

16. An assembly as in claim 15 further comprising a track means for guiding movement of said shield means relative to said locking means and including at least one track structure being elongated and integrally formed on said inner surface of said sleeve and including a first end and a second end each cooperatively configured and disposed to lockingly receive said projecting portion of said one finger therein.

17. An assembly as in claim 16 wherein at least one of said first and second ends of said one track structure is disposed contiguous to a receiving socket recessed inwardly into said inner surface of said sleeve a sufficient distance to receive said projecting portion of said one finger therein and further recessed inwardly a greater distance than a majority of the length of said track structure.

* * * * *